United States Patent [19]

Ogino et al.

[11] Patent Number: 5,090,416
[45] Date of Patent: * Feb. 25, 1992

[54] OPHTHALMOLOGICAL DIAGNOSIS METHOD AND APPARATUS

[75] Inventors: Kouji Ogino, Hino; Yoshihisa Aizu, Machida, both of Japan

[73] Assignee: Kowa Company, Ltd., Japan

[*] Notice: The portion of the term of this patent subsequent to May 10, 2005 has been disclaimed.

[21] Appl. No.: 364,488

[22] Filed: Jun. 9, 1989

Related U.S. Application Data

[63] Continuation of Ser. No. 165,817, Mar. 9, 1988, abandoned.

[30] Foreign Application Priority Data

Mar. 27, 1987 [JP] Japan .................. 62-71396

[51] Int. Cl.⁵ ............................................... A61B 5/02
[52] U.S. Cl. ............................... 128/691; 351/216
[58] Field of Search .................. 128/633–634, 128/637, 664–667, 691–694, 745; 356/39–41; 351/216–217

[56] References Cited

U.S. PATENT DOCUMENTS

| | | | |
|---|---|---|---|
| 4,157,708 | 6/1979 | Imura | 128/666 |
| 4,166,695 | 9/1979 | Hill et al. | 128/691 X |
| 4,305,398 | 12/1981 | Sawa | 128/666 X |
| 4,346,991 | 8/1982 | Gardner et al. | 128/691 X |
| 4,350,163 | 9/1982 | Ford, Jr. et al. | 128/745 X |
| 4,402,325 | 9/1983 | Sawa | 128/666 |
| 4,485,820 | 12/1984 | Flower | 128/634 X |
| 4,569,354 | 9/1986 | Shapiro et al. | 128/745 X |
| 4,702,576 | 10/1987 | Magnante | 128/745 X |
| 4,743,107 | 5/1988 | Aizu et al. | 128/691 X |

OTHER PUBLICATIONS

Cohen et al., "Multiple Scattering Analysis of Retinal Blood Oximetry", *IEEE Trans. on Biomed. Engr.*, vol. BME-23, No. 5, pp. 391–400, 9-1976.

"Monochromatic Ophthalmoscopy and Fundus Photography—the Normal Fundus", by F. C. Delori et al., *Arch Ophthalmol*, vol. 95, May 1977, pp. 861–868.

"Monochromatic Ophthalmoscopy and Fundus Photography—the Pathological Fundus", by N. M. Ducrey et al., *Arch Ophthalmol*, vol. 97, Feb. 1979, pp. 288–293.

*Primary Examiner*—Lee S. Cohen
*Assistant Examiner*—J. P. Lacyk
*Attorney, Agent, or Firm*—Bruce L. Adams; Van C. Wilks

[57] ABSTRACT

An ophthalmological diagnosis method and an apparatus for carrying out the method is disclosed. According to the invention, one of a plurality of laser beams is selected depending upon the tissue layers in the eye fundus to be diagnosed, and is projected thereon. Light is scattered by blood cells within a tissue layer of the eye fundus that depends upon the wavelength of the selected laser beam. The scattered light is received and photoelectrically converted into an electrical signal, which is then evaluated to measure the blood flow state within the tissue layer of the eye fundus.

21 Claims, 8 Drawing Sheets

He-Ne 543.5nm

He-Ne 543.5nm

Ar 514.5nm

Ar 514.5nm

Ar 514.5nm

He-Ne 594.1nm

He-Ne 594.1nm

He-Ne 594.1nm

He-Ne 632.8nm

He-Ne 632.8nm

He-Ne 632.8nm

OPHTHALMOLOGICAL DIAGNOSIS METHOD AND APPARATUS

This is a continuation of application Ser. No. 165,817, filed Mar. 9, 1988, now abandoned.

BACKGROUND OF THE INVENTION

1. Field of the Invention

This invention relates to an ophthalmological diagnosis method and an apparatus for carrying out this method, more particularly to an ophthalmological diagnosis method and apparatus whereby the eye fundus is illuminated by a beam of laser light and reflected laser light diffused by blood cells within the tissue of the eye is received and converted into an electrical signal which is analyzed to measure the state of the blood flow in the tissue of the eye fundus.

2. Description of the Prior Art

Conventional optical methods for measuring the state of the blood flow in the eye fundus include those disclosed in Japanese Patent Laying-open Nos. 58(1983)-118730 and 56(1981)-49134.

In the former method the light of a He-Ne laser (632.8 nm) is used to illuminate blood vessels of the eye fundus, and the frequency shift in the light reflected from the red blood cells produced by the Doppler effect is utilized to measure the velocity of the blood flow. However, the object of this method is to examine the surface blood vessels of the fundus, not the state of the blood flow in vessels which are located deeper in the fundus tissue. Moreover, although it is generally known that the degree of penetration of the laser light into the fundus tissue depends on the wavelength of the light, at present there is no selection of a suitable wavelength that takes this characteristic into consideration.

With the latter method the fundus is illuminated by visible light with a wavelength of 550 nm to 650 nm reflected from the pigmented layer of the retina, and near-infrared light in the 700 nm to 1,000 nm range selected from light having a wavelength that is longer than 610 nm reflected back after having reached the choroid layer, and pulse waves are obtained from visible reflected light from the fundus that indicates the retinal blood flow state, and from near-infrared reflected light that indicates the choroid blood flow rate, allowing ailments of the fundus to be determined from the result of a comparison of the two pulse waves. With this method, it is not possible to evaluate one blood flow state, retinal or choroid, independently of the other. In addition, although there are a number of tissue layers in the retina, the apparatus of the method does not distinguish between layers in the blood flow evaluation.

Another method of measuring the blood flow state involves directing a laser beam of a prescribed diameter onto the fundus to produce a laser speckle pattern formed by reflected light diffused by the fundus tissue, and by analyzing movement in the speckle pattern detected as fluctuations in the intensity of the light, the state of the blood flow in the eye fundus is determined, a method in respect of which the present inventors have submitted a patent application (Appln. No. 61(1986)-38240). Again, with the said method the fundus tissue layer to be measured is not clearly defined, in addition to which consideration is not given to selection of a laser light source having a suitable wavelength. Because of this, which of the eye fundus tissue layers are being measured is unclear.

SUMMARY OF THE INVENTION

It is therefore an object of the present invention to provide an ophthalmological diagnosis method and apparatus enabling accurate and effective measurement of the state of blood flow in various tissue layers in the eye fundus under ophthalmological examination.

According to the present invention, the eye fundus is illuminated with a laser beam, light scattered by blood cells within the tissue of the eye fundus is received, photoelectrically converted into an electrical signal, and evaluated to measure the blood flow state within the tissue of the eye fundus, and the wavelength of the laser beam is made variable in accordance with the tissue layers of the eye fundus to be diagnosed.

By utilizing the wavelength dependency of the scattered light on the tissue layers of the fundus, the wavelength range of the laser light source employed for the measurement can be specified for each fundus tissue layer that is to be measured. Therefore the laser light wavelength can be varied in accordance with which of the tissue layers of the fundus is to be examined, thereby enabling the blood flow state in the said tissue layer to be measured accurately.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

The invention will now be described in detail with reference to the drawings.

Figure 1:
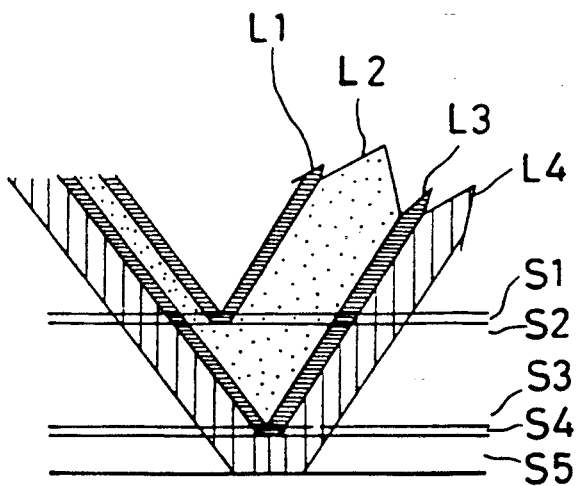
FIG. 1 is an explanatory diagram showing the scattered light wavelength characteristic for each tissue layer of the eye fundus.

The present invention utilizes the relationship between eye fundus tissue layer and the wavelength of light scattered therefrom. It is generally known that, as shown in FIG. 1, light L1 having a wavelength shorter than 530 nm beamed at the fundus is scattered by the nerve fiber layer S1 of the retina; light L2 having a wavelength in the range of approximately 540 nm to 580 nm is scattered by the ganglion cell layer S2 of the retina and the rod cone layer S3 of the retina; light L3 having a wavelength in the range of approximately 580 nm to 620 nm is scattered by the pigmented layer S4 of the retina; and light L4 having a wavelength longer than about 610 nm is scattered by the choroid layer S5. With ophthalmological diagnostic apparatuses that measure blood flows in the eye fundus based on the light scattering characteristics of living tissue, in order to ensure that the measurement is of the required tissue layer, light in certain wavelength ranges that can contain information from more than one layer is excluded. For example, the range 610 nm to 620 nm would contain a combination of information relating to the choroid layer and the retina. Also, the following laser beam wavelengths L1 to L4 have been established to provide some latitude in the wavelengths used to further ensure that the measurement is directed at the required tissue layer.

L1: A wavelength shorter than 530 nm for measuring the blood flow state in the nerve fiber layer S1 of the retina.

L2: A wavelength in the range 540 nm to 570 nm for measuring the blood flow state in the ganglion cell layer S2 and the rod cone layer S3 of the retina.

L3: A wavelength in the range 580 nm to 600 nm for measuring the blood flow state in the pigmented layer S4 of the retina.

L4: A wavelength longer than 630 nm for measuring the blood flow state in the choroid layer S5.

Conventional eye fundus blood flow measurement apparatuses have not given adequate consideration to the wavelength of the measuring light beam. As a consequence, even when the object has been to measure the blood flow state in the retina, it is mainly He-Ne lasers (wavelength: 632.8 nm) that have been utilized although such lasers are only suitable for measuring the blood flow state in the choroid layer. Because of this, these apparatuses are not the right ones to use for achieving the original objective. With the present invention, which of the wavelengths L1 to L4 is to be used may be selected in accordance with the tissue layer in which the blood flow state is to be measured, thereby ensuring that it is the blood flow state in the desired tissue layer that is measured.

For example, L1 lasers include a He-Cd+ laser with a wavelength of 441.6 nm, Ar+ lasers with a wavelength of 457 9 nm, 476.5 nm, 488.0 nm, 496.5 nm or 514.5 nm, and Kr+ lasers with a wavelength of 476.2 nm or 520.8 nm; for L2 there are a 594.1 nm He-Ne laser and a 568.2 nm Kr+ laser; for L3 there are a 543.5 nm He-Ne laser and a 568.2 nm Kr+ laser; and for L4 there are a 632.8 nm laser, a 636.0 nm He-Cd+ laser and a 647.1 nm Kr+ laser. To take one example, a light beam source with an L2 wavelength would be appropriate for measuring the blood flow state in the retina, and on the basis of performance, cost and ease of use, a 543.5 nm He-Ne laser would be suitable.

Use of a measuring laser beam source that has just one wavelength helps to define the tissue layer in which the blood flow state is to be measured. However, equipping an eye fundus blood flow apparatus with measuring laser beam source means possessing two or more wavelengths enables the person performing the ophthalmological examination to select the target for the blood flow state measurement by selecting the measuring light wavelength.

The operating arrangement of the apparatus according to the invention for selecting the measuring light wavelength and performing ophthalmological diagnosis will now be explained with reference to FIGS. 2, 3 and 5.

Figure 2:
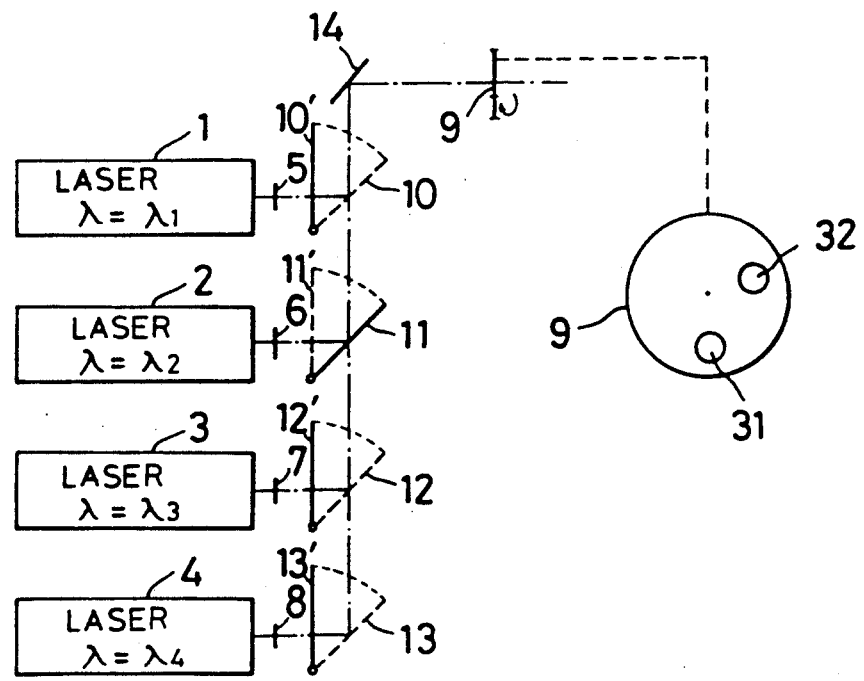
FIG. 2 is a block diagram illustrating the working principle of the arrangement according to the present invention.

In the embodiment shown in FIG. 2, reference numerals 1 to 4 denote laser beam light sources which generate respective laser beams of different wavelength $\pi 1$ to $\lambda 4$ (corresponding to the aforementioned L1 to L4). Laser beams from the laser beam sources are passed through respective light intensity adjustment filters 5 to 8 for attenuating the beam in accordance with considerations of the laser beam induced damage threshold value of the fundus tissue for the wavelength concerned and the various safety standards, and then impinge on swingable mirrors 10 to 13. To select a specific laser beam wavelength, for example $\lambda 2$, the corresponding swingable mirror (in FIG. 2, swingable mirror 11) would be inserted into the light path. The laser beam reflected by a swingable mirror is then reflected by a mirror 14 so as to impinge on a circular disk 9 which has a filter 31 and an aperture 32 disposed around its periphery. For system alignment purposes prior to the blood flow measurement the filter 31 is moved into the light path to reduce the laser beam intensity, while for blood flow measurement the aperture 32 is moved into the light path to provide a laser beam of the requisite high intensity.

Figure 3:
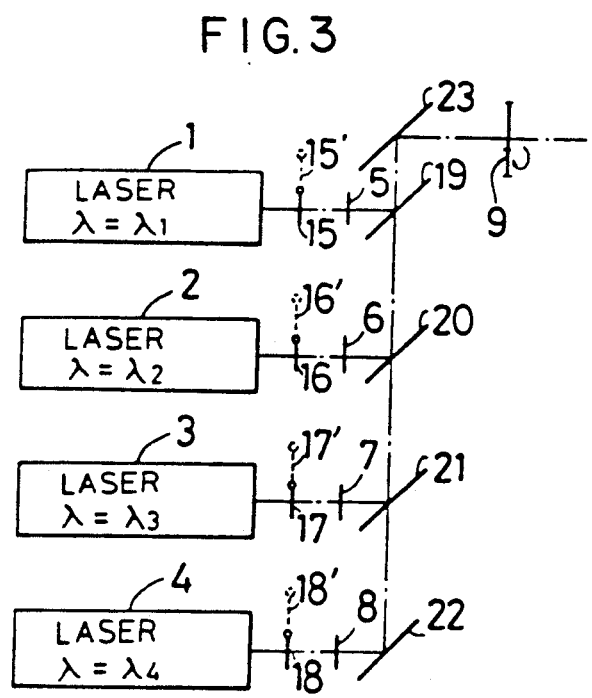
FIG. 3 is a block diagram illustrating the working principle of another arrangement according to the present invention.
Figure 4A:
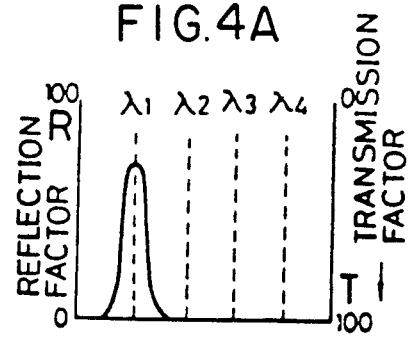
FIGS. 4(A) to 4(D) are spectral characteristic curves of wavelength separation mirrors.
Figure 4B:
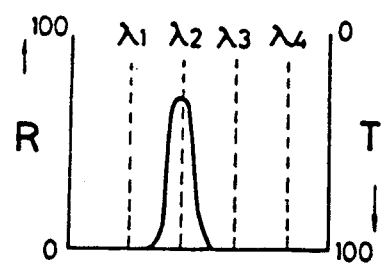
Figure 4C:
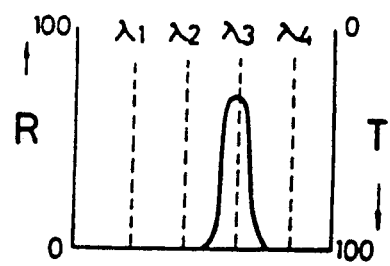
Figure 4D:
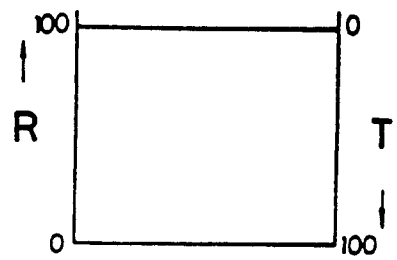

FIG. 3 shows an embodiment in which a wavelength separation mirror is used for selecting a laser beam wavelength. In the figure, parts that are the same as those in FIG. 2 have the same reference numerals. In this embodiment, disposed in the light paths corresponding to laser beam sources 1 to 4 are wavelength separation mirrors 19 to 21 and mirror 22 respectively, which have the respective spectral characteristic curves shown in FIGS. 4(A) to 4(D). Also, shutters 15 to 18 are disposed between the laser beam sources 1 to 4 and filters 5 to 8. With this arrangement, to select a laser beam that has a wavelength $\lambda 2$, for example, shutter 16 is removed from the light path, whereby the laser beam of wavelength $\lambda 2$ is reflected by the wavelength separation mirror 20, transmitted by the mirror 19, reflected by the mirror 23 having the type of spectral characteristics shown in FIG. 4(D), and impinges on the circular disk 9 for selection of the wavelength $\lambda 2$ laser beam.

Figure 5:
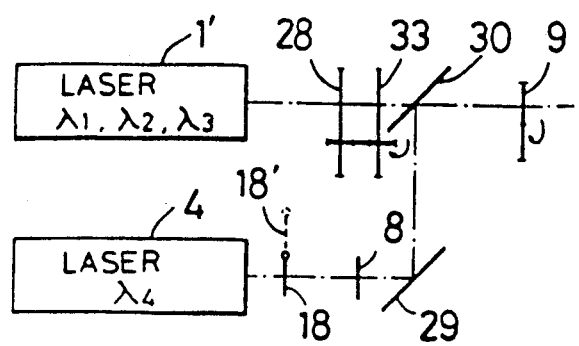
FIG. 5 is a block diagram illustrating the principle of another arrangement according to the present invention.
Figure 6:
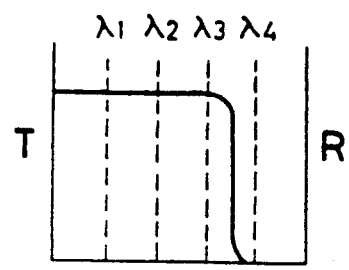
FIG. 6 is a characteristic curve showing laser light wavelength spectral characteristics.
Figure 7A:
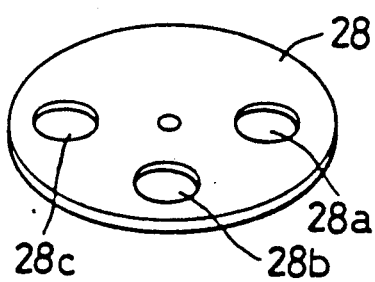
FIG. 7(A) is a perspective view of an interference filter member.
Figure 7B:
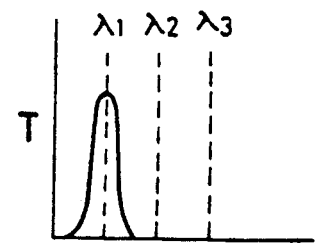
FIGS. 7(B) to 7(D) are curves showing the spectral characteristics of interference filters.
Figure 7C:
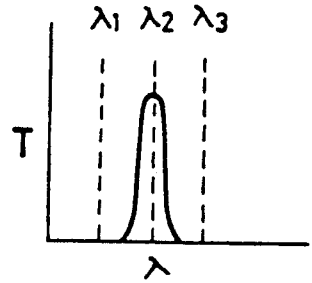
Figure 7D:
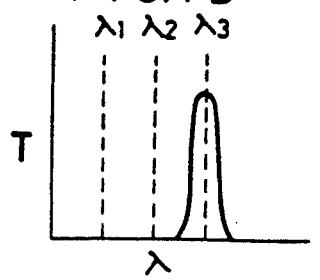

FIG. 5 shows an embodiment that employs a beam source for simultaneous multiple-wavelength laser beam production, and a beam source that generates z single wavelength laser beam. In the figure, parts that are the same as those in FIGS. 2 and 3 have the same reference numerals. Laser beams having the wavelengths $\lambda 1$ to $\lambda 3$ shown in FIG. 6 that are generated by the multiwavelength laser beam source 1' of FIG. 5 are passed through an interference filter member 28. As shown in FIG. 7(A), the interference filter member 28 is provided toward its periphery with interference filters 28a to 28c that have the spectral characteristics shown in FIGS. 7(B) to 7(D), each of said filters 28a to 28c transmitting only one of the laser beams from the beam source 1'. Provided to the rear of the interference filter member 28, and arranged to move in linked association therewith, is a filter 33 that, similarly to the filters 5 to 8, is for attenuating the laser beam.

The single wavelength λ4 beam generated by the laser beam source 4 is guided to a mirror 29 via the shutter 18 and the filter 8. A wavelength separation mirror 30 has spectral characteristics that cause it to transmit light from the multiwavelength laser beam source 1' and reflect light from the laser beam source 4.

With this arrangement, laser beam wavelengths λ1 to λ3 can be selected by rotating the interference filter member 28 and closing the shutter 18 located in front of the output mirror of the laser beam source 4. Laser beam wavelength λ4 generated by laser beam source 4 can be selected for measurement purposes by moving a portion of the interference filter member that has no interference filter into the light path and retracting the shutter 18 out of the light path to position 18'.

The filters 5 to 8 of FIGS. 2 and 3 may be omitted by appropriately setting the spectral characteristics of the swingable mirrors 10 to 13 shown in FIG. 2 and the wavelength separation mirrors 19 to 22 shown in FIG. 3. Also, the interference filter members 28 and 33 shown in FIG. 5 may be integrated into the type of form shown in FIG. 7(A), and the filter 33 may be omitted by setting the transmittance of the interference filter appropriately.

Figure 8:
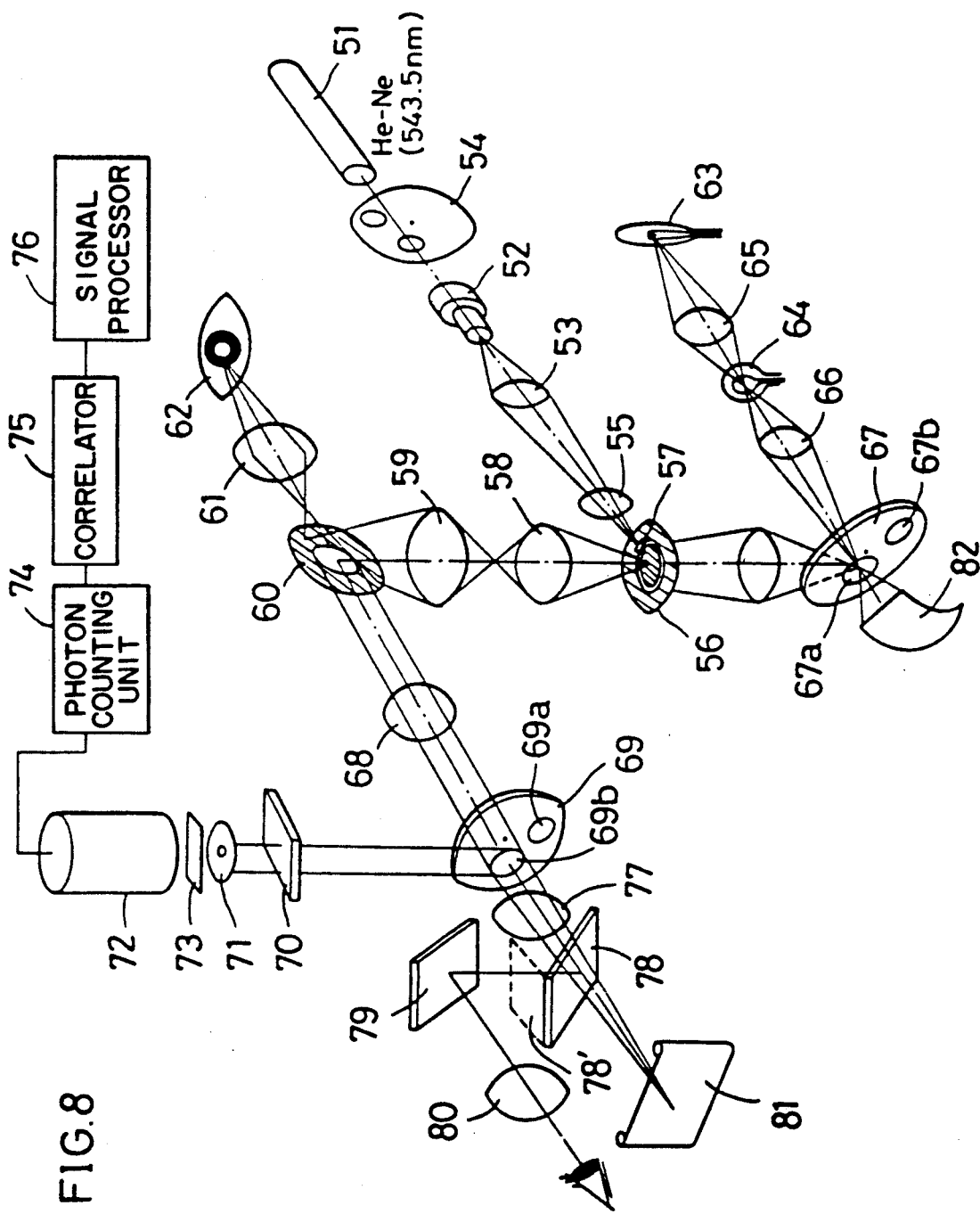
FIG. 8 is a perspective view of the arrangement of a first embodiment of the present invention based on the laser speckle phenomenon.

FIGS. 8 onwards show embodiments directed at measurement of retinal blood flow state using the above principle by utilizing, of the scattering phenomena, the laser speckle phenomenon.

With reference to FIG. 8, a laser beam source 51 is one that generates a laser beam of a wavelength that is appropriate to the measurement of the retinal blood flow state in the retina's nerve fiber layer and rod cone layer, a 543.5 nm He-Ne laser being one example of such a laser. The beam generated by the laser beam source 51 is passed through a light intensity adjustment filter 54 to adjust the intensity of the beam.

The light intensity adjustment filter 54 has two filters with different transmittances disposed along a circular locus having its center at the center of the circular disk. One is to lower the intensity of the laser beam to within the various safety standard; during the alignment process prior to blood flow measurement; and the other is to raise the intensity of the beam for use during the actual measurement of the blood flow. The intensity of the laser beam is thus adjusted by rotating the disk to select a filter. Also, by interposing a nonfilter portion of the disk into the light path, the disk can function as a shutter.

Next, the laser beam passes via a condenser lenses 52 and 53 and relay lens 55 into the eye fundus illuminating projector of the eye fundus camera. The laser beam guided by the relay lens 55 is reflected by a mirror 57 disposed at one part of the annular opening of a ring slip 56 in the eye fundus illuminating projector and thereafter passes along the same light path to the eye under examination 62 as that followed by the eye fundus observation and photographic light beams. As a result, the laser beam passes through the relay lenses 58 and 59, is reflected by a ring mirror 60, passes through an objective lens 61 and converges on the cornea of the eye under examination 62 to reach the eye fundus in a diverged state. The 543.5 nm laser beam is scattered by the ganglion cell layer S2 and rod cone layer S3 of the retina, as shown in FIG. 1, producing a speckle pattern. The speckle pattern involves light scattered by the blood cells flowing in the tissue that is being examined, so that the blood flow state can be measured by examining the behavior of the speckles in the speckle pattern.

This laser-illuminated area is also illuminated by the illuminating projector of the fundus camera so as to facilitate observation. The system for providing the illumination for observation is constituted of an observation light source 63 disposed on the same light path as a photographic light source 64, a condenser lens 65, a condenser lens 66, and a mirror 67a. As the path of the laser beam coincides with that of the team of observation light, the laser beam can be made to impinge on the desired region of the eye fundus in a plane perpendicular to the optical axis of the fundus by use of the mechanisms for swinging the eye fundus camera vertically and horizontally and also by use of the eye fixation mechanism.

By setting the wavelength of the measuring laser beam to an appropriate value it becomes possible to set the measurement region three-dimensionally, compared with the conventional two-dimensional setting.

Figure 9A:
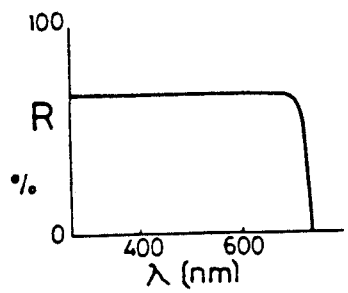
FIGS. 9 to 12 are characteristic curves showing the characteristics of wavelength separation means.
Figure 9B:
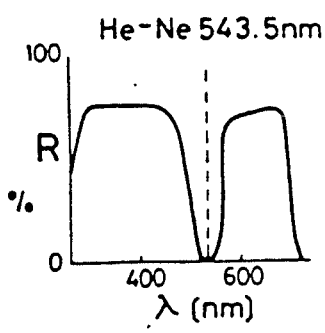

The mirror 67a has the spectral characteristics shown in FIG. 9(A). During blood flow measurement a change is made to a wavelength separation mirror 67b that, having the spectral characteristics shown in FIG. 9(B), separates out the same wavelength components as that of the laser beam contained in the observation and photographic light. The said components are transmitted through the wavelength separation mirror 67b and are absorbed by a light trap 82.

Figure 9C:
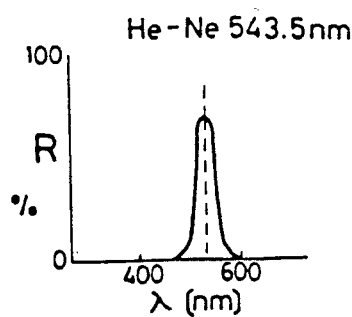

The speckle light containing the retinal blood flow information is again received by the objective lens 61, passes through the ring mirror 60 and a photographic lens 68 to reach a wavelength separation mirror 69. The wavelength separation mirror 69 has an aperture 69a of a diameter that is larger than that of the light beam, and a wavelength separation mirror 69b, disposed along a circular locus having its center at the center of the circular disk. The wavelength separation mirror 69b has the spectral characteristics illustrated by FIG. 9(C) and it therefore reflects most of the speckle light (green) generated by a He-Ne laser beam (543.5 nm). The aperture 69a is interposed in the light path when blood flow measurement is not being conducted, and the wavelength separation mirror 69b is interposed in the light path during blood flow measurement. The light reflected by the wavelength separation mirror 69b passes through an interference filter 70 and a detection aperture 71 to a photomultiplier 72 where it is detected. The interference filter 70 has the spectral characteristics shown in FIG. 9(C) which are in the same wavelength region as the spectral characteristics of the wavelength separation mirror 69b, so it passes only laser speckle light to the photomultiplier 72. A shutter 73 is disposed in front of the photomultiplier 72. The output from the photomultiplier 72 is converted to photon counting pulses by a photon counting unit 74 and the correlation function of output data obtained from the photon counting unit 74 is calculated by a correlator 75. The correlation thus obtained is analyzed by a signal processor 76 and the blood flow state is evaluated accordingly.

With this arrangement, observation light, photographic light and a slight amount of laser light transmitted through the wavelength separation mirror 69b is passed via a relay lens 77, a swingable mirror 78 and a mirror 79 to an eyepiece 80 through which it can be observed. Alternatively, the light passing through the wavelength separation mirror 69b can be directed for photographic purposes onto photographic film 81 by raising the swingable mirror 78 to the position indicated by the reference numeral 78'.

With the separation of the same wavelength components as that of the laser beam from the observation and photographic light by the wavelength separation mirror 67band the reflection of only the laser beam and the same wavelength components of observation and photographic light contained in the light scattered by the eye fundus by the wavelength separation mirror 69b, the photomultiplier 72 is enabled to receive, via the interference filter 70, only speckle light containing blood flow information. In addition, since the wavelength separation mirror 69b will pass a small amount of the light of the laser beam, the position at which the eye fundus blood flow state is being measured can be observed and photographed. Because the position illuminated by the laser beam can be directly observed by eye or photographed, it is also effective with respect to the recording of the measurement results.

Figure 10A:
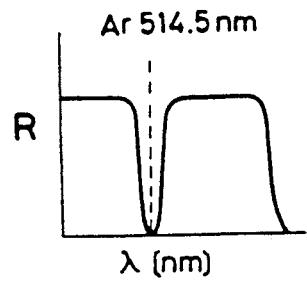
Figure 10B:
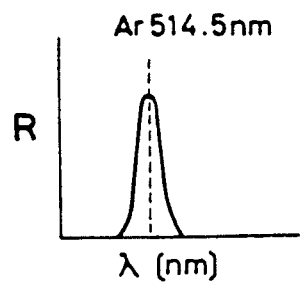
Figure 10C:
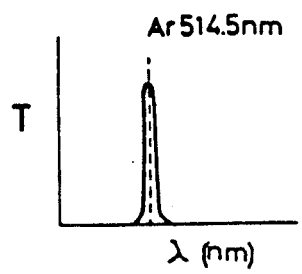
Figure 11A:
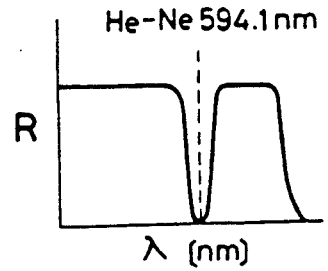
Figure 11B:
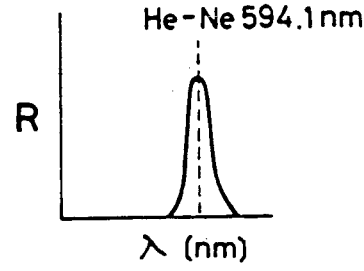
Figure 11C:
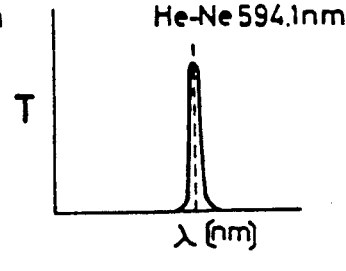
Figure 12A:
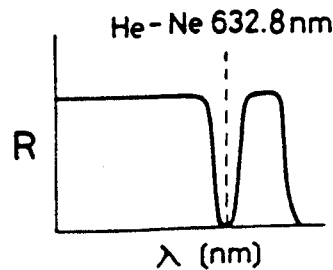
Figure 12B:
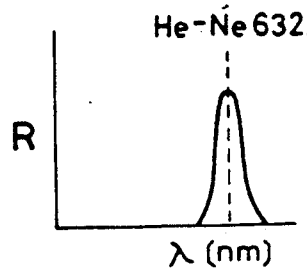
Figure 12C:
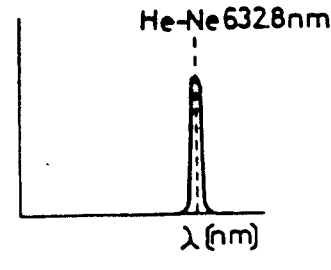

FIG. 8 shows an example of an apparatus for measuring the retinal blood flow state utilizing the laser speckle phenomenon. The wavelength of the laser beam generated by the laser beam source is decided based on a consideration of the depth of its penetration into living tissue. It is to be understood as a matter of course that if the wavelengths of the laser beam sources were changed accordingly, in combination with the wavelength separation mirrors 67b and 69b and the interference filter 70, it would be possible to measure the blood flow state of the nerve fiber layer of the retina in the case of the characteristics shown in FIGS. 10(A) to 10(C); of the pigmented layer of the retina in the case of the characteristics shown in FIGS. 11(A) to 11(C); and of the choroid layer in the case of the characteristics shown in FIGS. 12(A) to 12(C).

Figure 13:
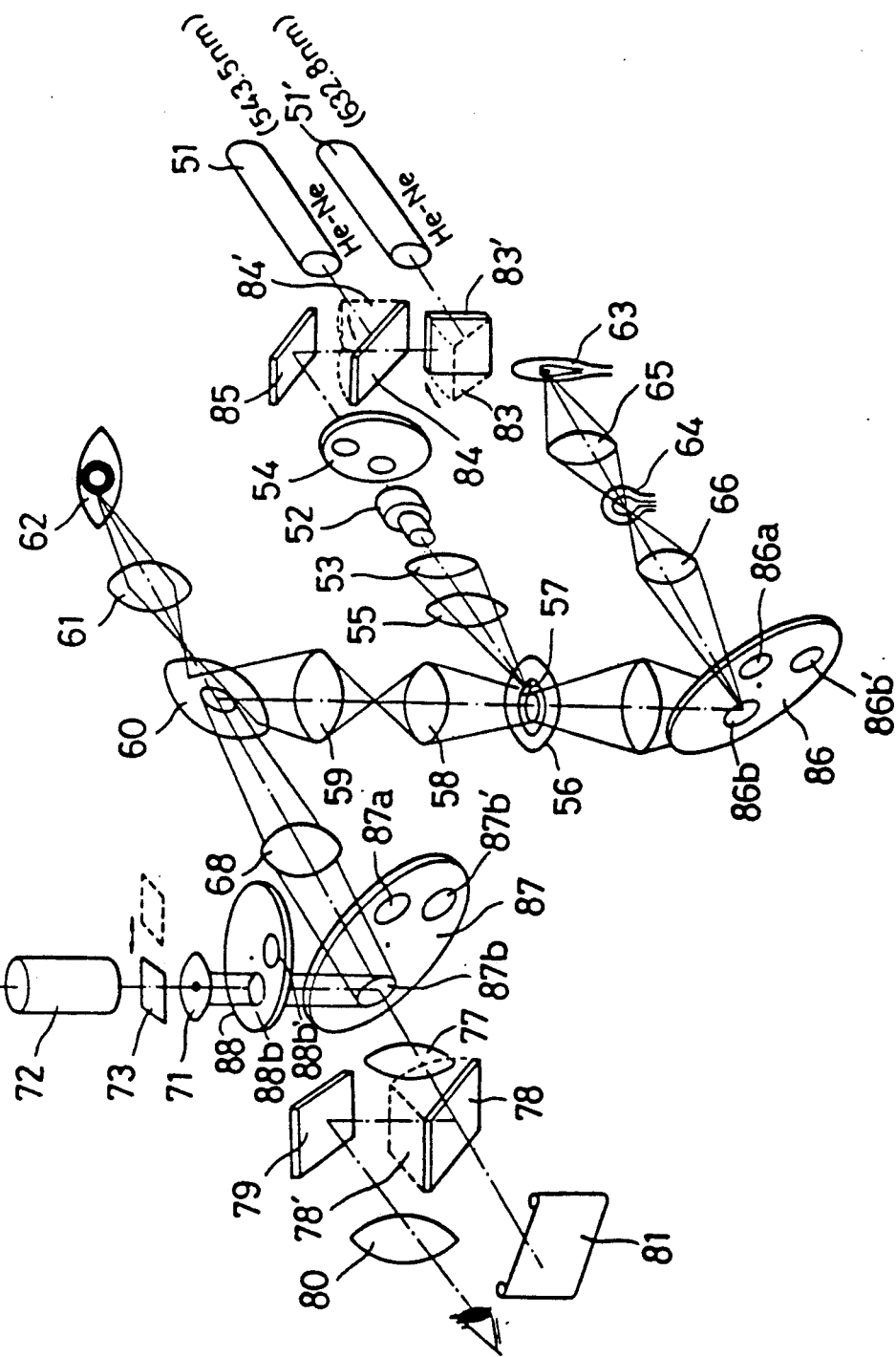
FIG. 13 is a perspective view of the arrangement of a second embodiment of the present invention based on the laser speckle phenomenon.

Again, as the measurement light source apparatus, in place of the laser beam source 51 shown in FIG. 8 the light source apparatus shown in FIGS. 2, 3 and 5 could be used to change the wavelength of the measurement laser beam, so that with just the one unit the required wavelengths could be selected depending on which eye fundus tissue layer was to be measured. An example of such an arrangement is shown in FIG. 13.

Figure 14:
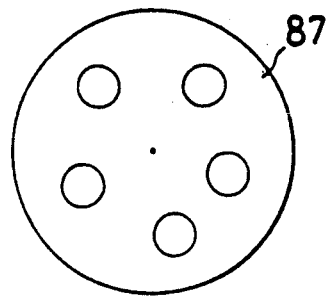
FIG. 14 is a perspective view of a wavelength separation mirror.
Figure 15:
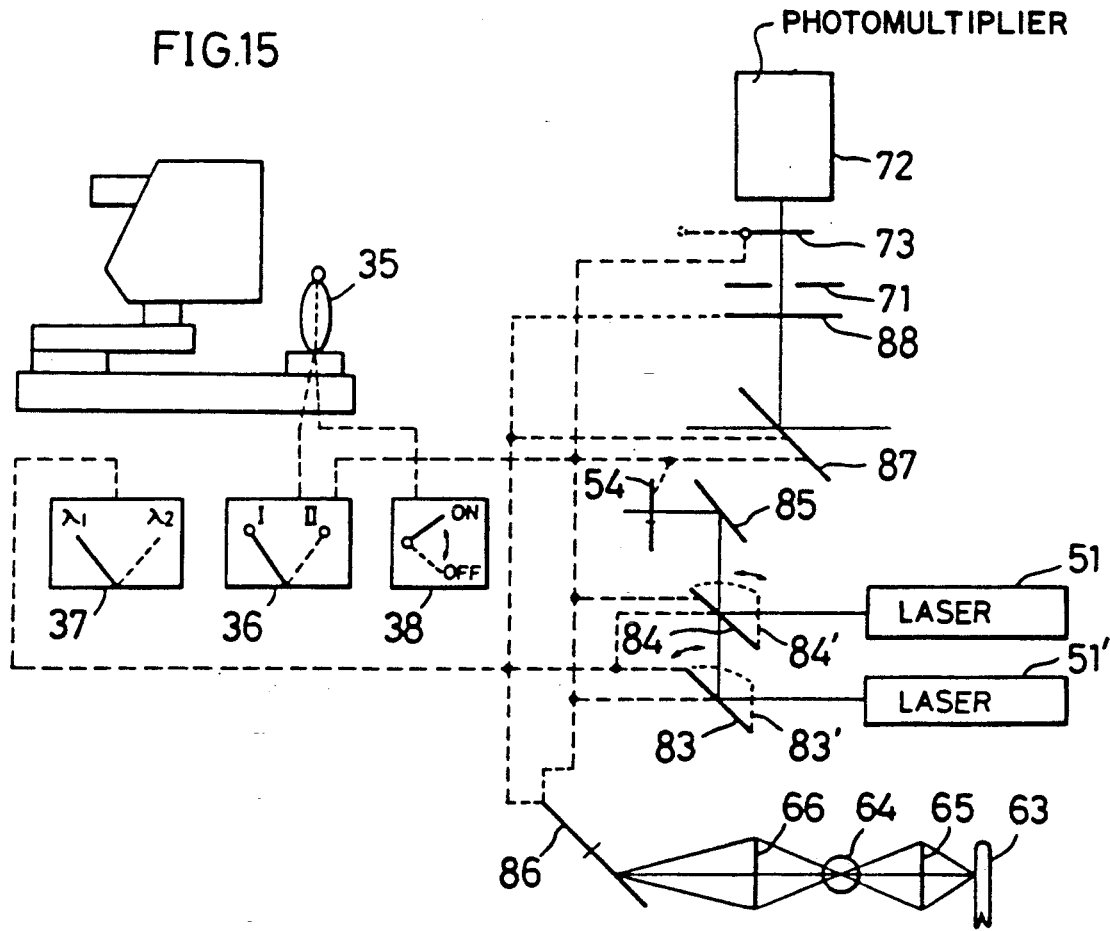
FIG. 15 is a diagram showing the arrangement of an embodiment equipped with fundus camera and blood flowmeter functions.

In this embodiment, in place of the unit 57 that includes the first wavelength separation mirror 67b, as along a circular locus having its center at the center of that have spectral characteristics whereby they transmit light having the same wavelength as that of the laser light source and reflect light having any other wavelength, and a mirror 86a that has uniform reflectance across the visible region. Also, in place of the second wavelength separation mirror 69 of FIG. 8, as shown in FIG. 14 there is employed a wavelength separation mirror 87 constituted of a circular disk and, disposed along a circular locus having its center at the center of the disk, wavelength separation mirrors 87b and 87b' that have spectral characteristics whereby they reflect light having the same wavelength as that of the measurement laser light source and transmit light having any other wavelength, and an aperture 87a with a diameter larger than that of the light beam and which is used to transmit all the light scattered from the fundus when the fundus is being observed, not measured. In addition, in place of the interference filter 70 of FIG. 8 there is a circular disk 88 as shown in FIG. 13 on which are disposed, along a circular disk, interference filters 88b and 88b' which transmit measurement laser beam source wavelength light. With this arrangement, linking the first and second wavelength separation mirror disks and the interference filter disk with the type of measurement laser beam wavelength selection means shown in FIGS. 2, 3 and 5 to permit switching thereof makes it possible to measure the blood flow state in a required tissue layer of the eye fundus and also enables the original functions of the eye fundus camera to be incorporated. FIG. 15 shows an example, described below, of an arrangement for the linking, with respect to the embodiment shown in FIG. 13.

As shown in FIG. 15, the apparatus according to this invention can function both as a fundus camera and as a blood flowmeter. To enable selection between these two types of operation, there is provided a switch 36 allowing selection between an eye fundus camera mode (hereinafter mode I) and a blood flow measurement mode (hereinafter mode II), which can be switched in the order mode I - mode II or in the order mode II - mode I. The apparatus is further provided with a switch 37. Setting the switch 37 according to the tissue layer to be measured causes the laser beam source with the required wavelength to be selected. In either of the modes I or II selected using switch 36, eye fundus photography can be enabled by turning on the eye fundus camera photography switch 38 and pressing switch 35.

The apparatus is arranged to be automatically in mode I when the main power is turned on. That is, on powering up the apparatus, with reference to FIG. 13, the swingable mirrors are in positions 83' and 84' so that the laser beam does not enter the observation or photography light path, and the shutter 73 in front of the photomultiplier is closed, prevention laser light impinging on the photomultiplier 40. Also, the mirror 86aon the first wavelength separation mirror disk 86 is interposed in the observation and photography path and the aperture 87a on the second wavelength separation mirror disk 87 is interposed in the light path. Therefore, the apparatus is in the state for functioning as an ordinary eye fundus camera.

When switch 36 is operated to select mode II, in accordance with the setting of the measurement laser beam wavelength selection switch 37, the swingable mirrors disposed in front of the laser beam sources are swung and the beam passed through the light intensity adjustment filter 54 to provide a laser beam of low intensity for observation or photography.

On the first wavelength separation mirror disk 86 the wavelength separation mirrors 86b and 86b' that reflect all light with a wavelength that differs from the wavelength of the laser beam source replace the uniform reflectance mirror 86a in the light path. Also, the wavelength separation mirrors 87b and 87b' on the second wavelength separation mirror disk 87 that only reflect speckle light scattered from the fundus are interposed in the light path instead of the aperture 87a. Also, at this point, interference filters 88b and 88b', selected the same way and which transmit only measurement laser beam source wavelength components, are inserted into the light path. In mode II, when the switch 35 is pressed, the shutter 73 in front of the photomultiplier 72 opens and the aperture of the light intensity adjustment filter 54 is inserted into the light path to pass a laser beam of a safe intensity into the observation and photography system, and the blood flow state is measured.

After the elapse of present measurement period, the shutter 73 of the photomultiplier 72 closes and the filter portion of the light intensity adjustment mirror 54 is inserted into the light path, thereby setting the intensity of the laser light to a low level.

Figure 16:
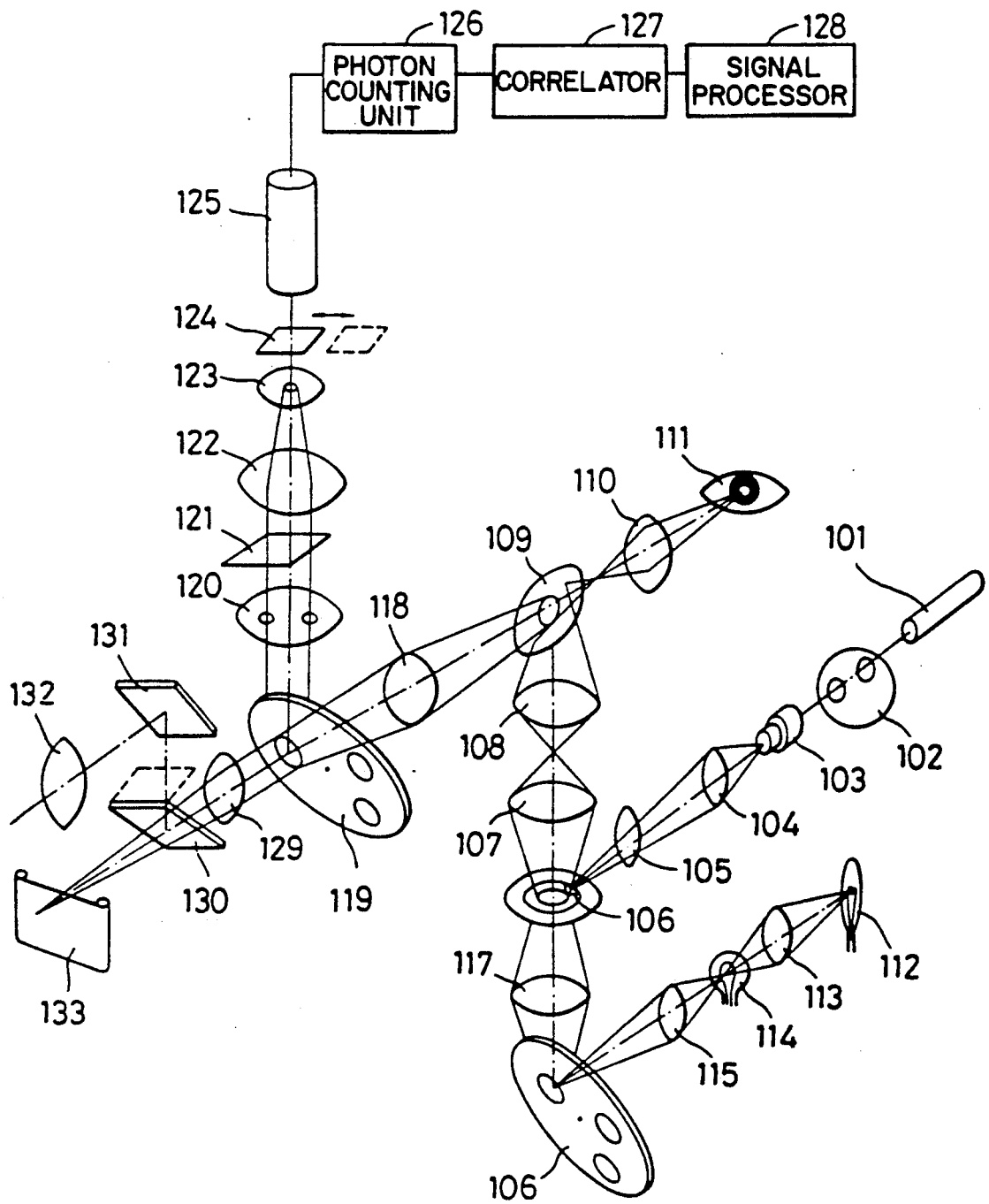
FIG. 16 is a perspective view of an embodiment based on the Doppler effect.

FIG. 16 shows an embodiment of the present invention in respect of a retinal blood flow measurement apparatus based on the prior-art Doppler effect. The difference compared with the retinal blood flow apparatus of FIG. 8 based on the laser speckle phenomenon lies in the optical constants of the lenses 103, 104 and 1(5 which are selected to adjust the laser beam used in retinal measurements to a beam diameter substantially equal to the diameter of the blood vessel concerned. In addition there are a double aperture 120, an imaging lens 122 and an aperture 123, which are means for extracting the Doppler shift frequency using heterodyne detection that are peculiar to apparatuses that utilize the Doppler effect. Other than these, the arrangement is the same as that shown in FIG. 8.

With respect to a) the ability to select the tissue layer to be measured, b) the ability to observe and photograph during measurements of the blood flow, and c) the inclusion of the flowmeter and eye fundus camera functions provided in accordance with the arrangement shown in FIG. 8, although the above arrangement utilizes a different light scattering phenomenon, utilization of the arrangement according to the present invention can be used to produce the same effect. This is because the present invention is not based on a specially designated light scattering phenomenon, whether the laser speckle phenomenon or the laser Doppler effect, but is instead based on the wavelength relationship of light scattered by the eye fundus. As such, although the foregoing explanation has been in respect to apparatus for measuring the blood flow state in the eye fundus based on the laser speckle phenomenon or the laser Doppler effect, in the case of the relation between wavelength and the depth of the eye fundus tissue layer from which the light is scattered being utilized to measure the blood flow state in a selected fundus tissue layer, no matter which light scattering phenomena the eye fundus flowmeter is based on, the present invention can be implemented and the effect that is the object of the invention attained.

While the invention has been described with reference to a preferred embodiment, it will be understood by those skilled in the art that various changes ma be made and equivalents may be substituted for elements thereof without departing from the scope of the invention. In addition, many modifications may be made to adapt a particular situation or material to the teachings of the invention without departing from the essential scope thereof. Thus, it is intended that the invention should not be limited to the particular embodiment disclosed as the best mode contemplated for carrying out the invention, but that the invention will include all embodiments falling within the scope of the appended claims.

What is claimed is:

1. An ophthalmological diagnosis method comprising the steps of:
    specifying one of a plurality of tissue layers in an eye fundus to be examined;
    illuminating the eye fundus with only a single laser beam of coherent light having a wavelength selected for the specified tissue layer so that coherent light scattered by blood cells in the illuminated tissue layer undergoes phase modulation corresponding to the movement of the blood cells to produce a speckle light pattern representative of the blood flow state in the specified tissue layer; and
    evaluating the fluctuations of the speckle light pattern to produce therefrom data representative of the blood flow state in the specified tissue layer of the eye fundus.

2. An ophthalmological diagnosis method according to claim 1 wherein, with respect to the tissue layers of the eye fundus, the step of illuminating comprises providing a laser beam with a wavelength not exceeding 530 nm for the nerve fiber layer of the retina; providing a laser beam with a wavelength in the range 540 nm to 570 nm for the ganglion cell layer of the retina and the rod cone layer of the retina; providing a laser beam with a wavelength in the range 580 nm to 600 nm for the pigmented layer of the retina; and providing a laser beam with a wavelength of 630 nm or longer for the choroid layer.

3. An ophthalmological diagnosis apparatus comprising:
    means for producing a plurality of laser beams of coherent light, each laser beam having a different wavelength corresponding to one of a plurality of tissue layers in an eye fundus;
    means for selecting one of said laser beams in dependence upon specifying one of the tissue layers of the eye fundus to be diagnosed;
    means for projecting said selected one of the laser beams to illuminate the specified tissue layer of the eye fundus so that coherent light scattered by blood cells within the illuminated tissue layer undergoes phase modulation corresponding to the movement of the blood cells to produce a speckle light pattern representative of the blood flow state in the specified tissue layer;
    means for receiving the coherent light scattered by blood cells within the illuminated specified tissue layer of the eye fundus; and
    means for evaluating the speckle light pattern of the coherent light scattered back from the specified tissue layer to measure the blood flow state within the specified tissue layer in the eye fundus.

4. An ophthalmological diagnosis apparatus according to claim 3, wherein the selecting means comprises a swingable mirror.

5. An ophthalmological diagnosis apparatus according to claim 3, wherein the selecting means comprises a wavelength separation filter, a wavelength separation mirror, and a shutter.

6. An ophthalmological diagnosis apparatus according to claim 3, wherein the means for producing the plurality of laser beams comprises a corresponding number of laser beam sources.

7. An ophthalmological diagnosis apparatus according to claim 3, wherein the means for producing the plurality of laser beams comprises a single laser beam source.

8. An ophthalmological diagnosis apparatus according to claim 3, further comprising means for providing light to observe and photograph the eye fundus, and means for removing the wavelength component of the selected laser beam from observation and photographic light.

9. An ophthalmological diagnosis apparatus according to claim 3, further comprising means for providing observation light and photographic light for observing and photographing the eye fundus, and means for detecting, selecting and separating the selected laser beam wavelength component from the laser beam, the observation light and the photographic light reflected and diffused by the eye fundus.

10. An ophthalmological diagnosis apparatus according to claim 9, wherein the selection and separation means has means for inserting same into and removing same from an optical path along which the laser beam, observation light and photographic light travel.

11. An ophthalmological diagnosis method comprising the steps of:

providing a plurality of beams of coherent light, each having a different wavelength corresponding to a different tissue layer in eye fundus;

illuminating a specified tissue layer with the beam having the wavelength corresponding to the specified tissue layer so that coherent light scattered by blood cells within the illuminated tissue layer undergoes phase modulation corresponding to the movement of the blood cells to produce a speckle light pattern representative of the blood flow state in the specified tissue layer; and evaluating the speckle light pattern of the scattered coherent light to measure the blood flow state in the specified tissue layer.

12. The method according to claim 11, wherein the beams of coherent light are laser beams and the step of evaluating comprises evaluating fluctuations of the speckle light pattern.

13. The method according to claim 11, wherein the step of providing comprises providing a laser beam with a wavelength not greater than 530 nm for the nerve fiber layer of the retina, a laser beam with a wavelength in the range 540 nm to 570 nm for the ganglion cell layer of the retina and the rod cone layer of the retina, a laser beams with a wavelength in the range 580 nm to 600 nm for the pigmented layer of the retina and a laser beam with a wavelength of not less than 630 nm for the choroid layer.

14. An apparatus for measuring the blood flow state in a specific one of the tissue layers of a patient's eye fundus, comprising: means for producing a laser beam of coherent light having a wavelength effective to be reflected at a specific one of the tissue layers in the eye fundus; means for projecting the laser beam onto the eye fundus to illuminate a specific tissue laser thereof corresponding to the wavelength of the laser beam so that coherent light scattered by blood cells in the illuminated tissue layer undergoes phase modulation corresponding to the movement of the blood cells to produce a fluctuating speckle light pattern representative of the blood flow state in the specific tissue layer of the eye fundus; and means receptive of the coherent light scattered at the specific tissue layer for measuring the fluctuations of the speckle light pattern and producing output data representative of the blood flow state in the specific tissue layer of the eye fundus.

15. An apparatus according to claim 14; wherein the means for producing a laser beam comprises means for producing a plurality of laser beams of coherent light, each laser beam having a wavelength effective to be reflected at a different one of the tissue layers in the eye fundus.

16. An apparatus according to claim 15; including means for selecting one of the laser beams whose wavelength corresponds to a desired tissue layer to be illuminated for projection onto the eye fundus.

17. An apparatus according to claim 16; wherein the means for selecting comprises displaceable mirrors selectively displaceable into and out of the paths of the laser beams for selecting one of the laser beams for projection onto the eye fundus.

18. An apparatus according to claim 16; wherein the means for selecting comprises sets of a wavelength separation filter, a wavelength separation mirror and a shutter disposed along the paths of the laser beams for selecting one of the laser beams for projection onto the eye fundus.

19. An apparatus according to claim 15; wherein the means for producing a plurality of laser beams comprises a plurality of laser beam sources.

20. An apparatus according to claim 15; wherein the means for producing a plurality of laser beams comprises a single laser beams source selectively operable in different modes to produce the plurality of laser beams.

21. An apparatus according to claim 14; including means for producing an observation light to enable observation of the eye fundus and a photographic light to enable photographing of the eye fundus, and means for separating the scattered coherent light which defines the speckle light pattern from the observation light and photographic light.

* * * * *